(12) United States Patent
Benavides Pérez et al.

(10) Patent No.: US 9,872,500 B2
(45) Date of Patent: *Jan. 23, 2018

(54) ADDITIVE FOR COATINGS CONTAINING METALLIC NANOPARTICLES

(71) Applicant: Servicios Administrativos Peñoles S.A. de C.V., Torreón, Coahuila (MX)

(72) Inventors: Ricardo Benavides Pérez, Torreon Coahuila (MX); José Gertrudis Bocanegra Rojas, Coahuila (MX); Jesús Manuel Martinez Martinez, Coahuila (MX); Julio César Rangel Mata, Coahuila (MX)

(73) Assignee: Servicios Administrativos Peñoles S.A. de C.V., Torreón, Coahuila (MX)

( * ) Notice: Subject to any disclaimer, the term of this patent is extended or adjusted under 35 U.S.C. 154(b) by 172 days.

This patent is subject to a terminal disclaimer.

(21) Appl. No.: 14/451,275

(22) Filed: Aug. 4, 2014

(65) Prior Publication Data

US 2016/0029640 A1   Feb. 4, 2016
US 2016/0330973 A9   Nov. 17, 2016

Related U.S. Application Data

(63) Continuation of application No. 12/741,327, filed as application No. PCT/MX2007/000134 on Nov. 5, 2007, now Pat. No. 8,796,364.

(51) Int. Cl.

| C09D 5/14 | (2006.01) |
|---|---|
| C09C 1/00 | (2006.01) |
| A01N 59/16 | (2006.01) |
| C09D 5/18 | (2006.01) |
| C09D 5/00 | (2006.01) |
| C09D 7/12 | (2006.01) |
| C09D 1/00 | (2006.01) |
| A01N 59/20 | (2006.01) |

(52) U.S. Cl.
CPC ............ *A01N 59/16* (2013.01); *A01N 59/20* (2013.01); *C09D 1/00* (2013.01); *C09D 5/00* (2013.01); *C09D 5/14* (2013.01); *C09D 5/18* (2013.01); *C09D 7/1216* (2013.01); *C09D 7/1266* (2013.01)

(58) Field of Classification Search
CPC ............ C09C 1/00; C09D 1/04; C09D 1/043
See application file for complete search history.

(56) References Cited

U.S. PATENT DOCUMENTS

| 8,796,364 B2 * | 8/2014 | Benavides Perez ... | B82Y 30/00 524/406 |
|---|---|---|---|
| 2010/0221525 A1 * | 9/2010 | Jonschker ............ | B82Y 30/00 428/327 |

FOREIGN PATENT DOCUMENTS

| DE | 102005056621 A1 * | 5/2007 | ............ B82Y 30/00 |
|---|---|---|---|
| GB | WO 2007144576 A2 * | 12/2007 | ............ C08J 3/226 |
| MX | CA 2704574 A1 * | 5/2009 | ............ B82Y 30/00 |

* cited by examiner

*Primary Examiner* — Brieann R Fink
(74) *Attorney, Agent, or Firm* — Michael J. Brown

(57) ABSTRACT

The additive of the present invention is intended for transferring, to a final coating, biocidal, UV protection, and flame retardant properties and in general the selected properties intrinsic to the metals and compounds of Ag, Au, Cu, Mg, Zn, Bi, Sb, said additive includes the use of solvents, surfactants, dispersants and resins that make it compatible with the final coating. Said coating treated with additive ensures perfect distribution and dispersion of the nanoparticles throughout it, without the need to be subjected to an inorganic substrate.

16 Claims, 1 Drawing Sheet

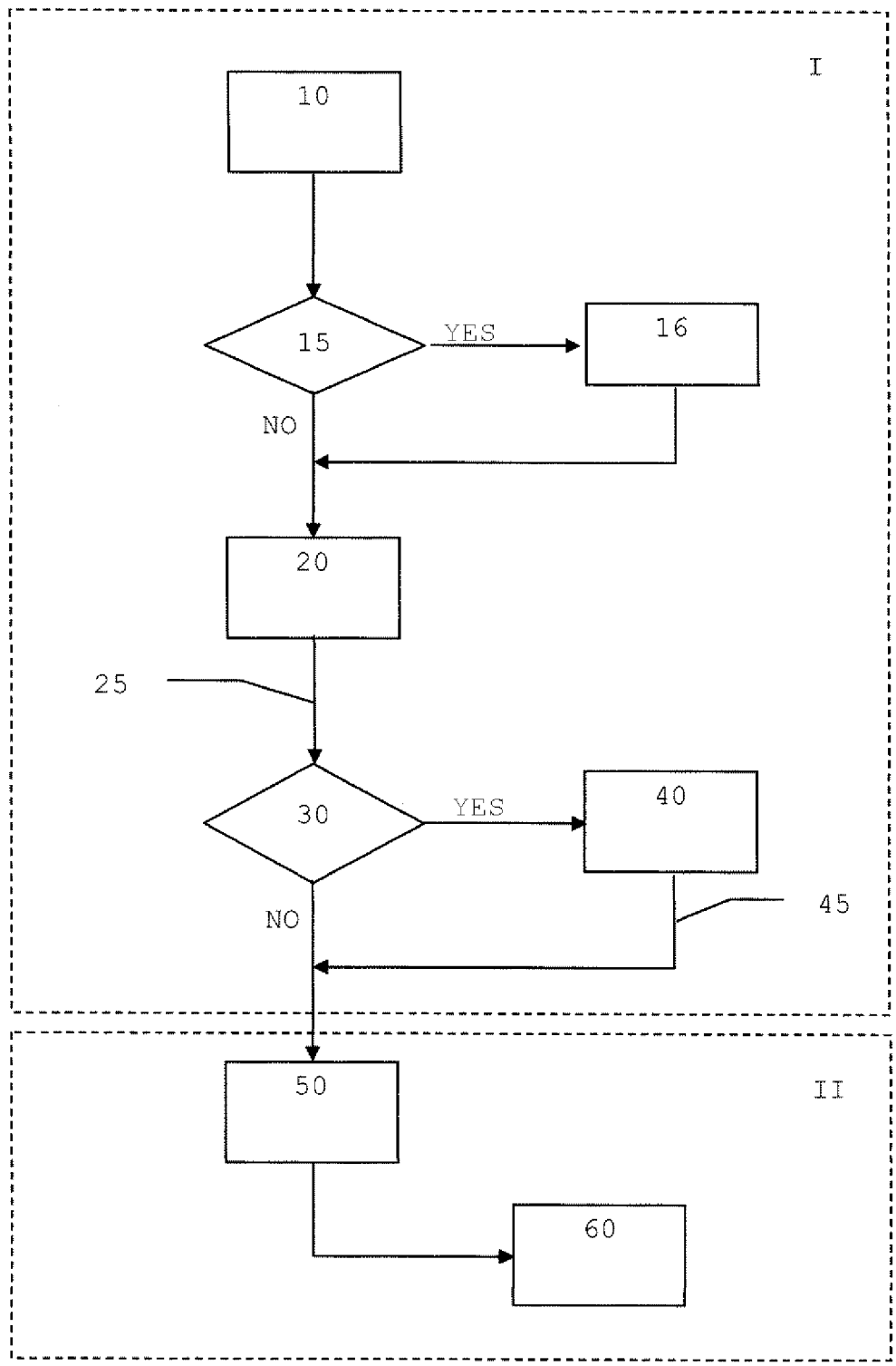

ADDITIVE FOR COATINGS CONTAINING METALLIC NANOPARTICLES

The application is a divisional of U.S. application Ser. No. 12/741,327, now U.S. Patent No. which is scheduled to issue on Aug. 5, 2014, which parent application claims priority from PCT Application No. PCT/MX2007/000134, filed on Nov. 5, 2007.

TECHNICAL FIELD OF THE INVENTION

The present invention relates to additives that are used in paints and coatings, for the purpose of endowing them with desirable properties in relation to the final application, in particular the invention relates to an additive that contains nanoparticles of one or more compounds, preferably metallic, where the solvents, dispersants and surfactants that accompany them are selected depending on the nature of the paint or coating.

BACKGROUND OF THE INVENTION

The use of nanoparticulate compounds for modifying properties different from that of the intrinsic nature of paints, varnishes and coatings in general is known and has increased considerably in recent years.

For example, it is known that nanoparticles of metallic silver are used for conferring antibacterial properties on the materials in which they are incorporated, as is shown in the patents cited hereunder.

The use of some metals or their compounds, as agents that help to improve some of the desired properties in products such as coatings, paints and other polymeric mixtures, is common in everyday practice, for example, the use of silver as antibacterial is well known, and it is known that their effect improves substantially when they are of nanometric size. Although materials exist in which nanometric metallic silver is incorporated, said silver is deposited on inert substrates with a size of several microns, resulting in localized zones with a high concentration of nanoparticles.

Zinc oxide is known for its fungicidal effect, and is widely used in personal hygiene articles and skin medications. It is also known that in nanometric sizes it can absorb ultraviolet light, offering protection for materials that contain it. As with all nanometric compounds, better dispersion and controlled particle size offer advantages, since unprotected zones are practically eliminated.

The flame retardant effect of magnesium hydroxide is also known, and it has been observed that in nanometric sizes it offers advantages, for example of transparency, without affecting the mechanical properties of the coating in which it is used. This is embodied in patent application PCT/MX 2007/000046 (Martinez et al., 2007), which relates to a method for the preparation of a flame retardant additive for coatings and the resultant products.

Similarly, the properties of nanoparticles of Ag, Au, Cu, Bi, Mg, Zn, Sb, their oxides, hydroxides, sulfides, chlorides, sulfates, and mixtures thereof, are transferred to the coating of the final application.

Several examples have been found of coatings in which nanoparticles are incorporated to endow them with certain qualities or properties. The main problem to be tackled is the efficient dispersion of the nanoparticles in the application volume, because of the appearance of agglomerates that reduce their effectiveness.

The present invention describes an additive that ensures the homogeneous distribution and efficient dispersion of the nanoparticles throughout the coating. For greater clarity, in this document "additive" means a mixture or combination of components that is added to another substance to give it qualities that it lacks or to improve those that it already possesses. In particular the additive according to the invention is for application in coatings such as paints, varnishes and polymeric mixtures that are fluid at room temperature.

In the prior art there is a great variety of alternatives for incorporating nanoparticles in coatings, and thus provide them with certain properties intrinsic to said nanoparticles, some examples of which are mentioned below.

Patent CN 1850924 (Li, 2006) describes the production of an antibacterial coating containing silver nanoparticles. The additive is prepared using hydroxylated acrylic resin or an emulsion of acrylic acid polymer, starting from a 6% solution of silver nanoparticles in a polyethylene wax. The product obtained in this method cannot be made compatible with other systems and is limited to a maximum concentration of 6%.

Patent CN 1837035 (Wang et al., 2006) gives an account of a method of preparation of a hybrid carbon membrane that contains inorganic nanoparticles. The product of this invention is limited to just one type of application.

Patent JP 2005248136 (Ando, 2005) discusses an additive that contains nanometric silver for coatings, which prevents marine organisms adhering to surfaces. This invention is limited to the removal of marine organisms on surfaces submerged in water and to a paint for marine application.

Patent TW 220398 (Liang, 2004) discusses an additive that contains metallic nanoparticles, but which are synthesized directly in an organic solvent. Application of the product of this invention is limited to materials compatible with organic solvents and that can be synthesized therein.

Patent WO 2003103392 (Nonninger et al. 2003) describes a coating that contains antibacterial metallic nanoparticles, but has the limitation that said nanoparticles are on other particles of titanium dioxide.

Publication US20070173564A1 (Sohn et al., 2007) relates to a composition for producing a transparent coating with a photocurable resin, which contains silver nanoparticles. The product of this invention is limited to silver nanoparticles in a photocurable transparent coating.

Publication US2006155033A1 (Sisson, 2006) describes an emulsion used for improving the electrical conductivity between contact surfaces, for example electrical connectors, and for protecting them against the effects of time. This coating is limited to the transfer of electrical properties and to the use of silver nanoparticles.

U.S. Pat. No. 6,855,749B1 (Yadav et al. 2005) is limited to a nanocomposite polymer that is mainly used as a material for biological uses in applications such as vehicles of medicinal products, biomedical devices, and implants of bones or teeth.

U.S. Pat. No. 6,228,904B1 (Yadav et al. 2001) relates specifically to a polymeric composite with nanomaterials with properties of resistivity, the method and the application of the mixture for producing a plastic with electrical properties. The teaching of this document is not directly applicable to fluid mixtures for coatings, as in our case, except that the properties in question are related to the electrical properties.

The additive of the present invention is designed for transferring, to a final coating, biocidal, UV protection, and flame retardant properties, and in general, selected properties intrinsic to the metals and compounds of Ag, Au, Cu, Mg, Zn, Bi, Sb; the additive includes the use of solvents, surfactants, dispersants and resins that make it compatible with the final coating. Said coating with additive ensures perfect distribution and dispersion of the nanoparticles throughout it, without the need for an inorganic substrate. The process for the manufacture of the additive starts from existing nanoparticles of the aforementioned metals and compounds, which can be in aqueous organic media or alternatively as dry powders, and are submitted to a treatment that allows them to be incorporated in coatings used in a wide variety of environmental conditions. The process can be used for obtaining a variety of functionalized additives.

OBJECTS OF THE INVENTION

One object of the present invention is to provide a composition for use as an additive in polymeric mixtures, such as paints, varnishes or coatings of a fluid nature, in which the properties desired in the final application are provided by metallic nanometric particles and their composites, selected specifically.

Another object of the present invention is that the nanoparticles of the additive that confer the properties on the coating are distributed homogeneously in the volume of the coating.

Another object of the present invention is to provide an additive in which the nanoparticles of the additive do not agglomerate, remaining dispersed throughout the shelf life, both of the additive and of the coating in which they are incorporated.

One more object of the present invention is that the properties desired in the coating can be obtained by the appropriate selection of nanoparticles of one or more metals and their compounds.

Yet another object of the present invention is to provide an additive in which the nanoparticles of metal or metal compounds do not require an additional carrier, such as ceramic materials, in order to remain unagglomerated.

These and other objects will become clear, to a person skilled in the art, on reading the description that follows.

BRIEF DESCRIPTION OF THE DRAWINGS

FIG. 1 is a block diagram that represents the process for production of the additive according to the invention.

DETAILED DESCRIPTION OF THE INVENTION

The additive prepared according to the method of the present invention is produced starting from metallic nanoparticles and their composites, with an average particle size that is selected in the range from 1 to 100 nanometers, preferably monodispersed, i.e. having a very narrow size variation, the particle size being a function of the desired application; for example, it is considered that in applications of the medical type, sizes less than 10 nm are preferred, and in UV protection sizes around 60 nm are preferred; and with a purity of at least 95%.

Selection of the material of the nanoparticles to be used in the formulation of the additive of the present invention is closely linked to the property that is desired in the final application, as can be seen from Table 1, which shows some examples that serve for determining the parameters recommended for obtaining the desired effects in the final application.

TABLE 1

Recommended selection of nanoparticles for preparation of the additive.

| Property | Ag° | Au° | Cu° | Bi° | Mg(OH)$_2$ | ZnO | AgS | Bi$_2$O$_3$ | Sb$_2$O$_5$ |
|---|---|---|---|---|---|---|---|---|---|
| A | X | | X | | | X | X | | |
| B | | | | | X | X | | X | |
| C | | | | | X | | | X | |
| D | X | | X | | | X | | | |
| E | X | X | X | X | | | | X | X |
| F | | | | X | X | X | | X | |

Where:
A: biocidal properties, such as bactericide, fungicide and algicide.
B: UV protection.
C: Flame retardant.
D: Fungicide.
E: Electrical conductivity.
F: Optical properties.

The nanometric particles selected according to Table 1 are submitted to a treatment for incorporating them in the final coating, for which it is possible to start from nanoparticles in aqueous, organic suspension or in powder form, without the compatibility between the vehicle of the nanoparticle and the base of the additive that is to be formulated being limiting, since an important part of the present invention is changing the vehicle in the additive to make it compatible with the final coating.

Referring to FIG. 1, which is a block diagram of the process for production of the additive of the invention, there are two zones, referenced with the numerals I and II: the first, made up of blocks (10) to (40), which represent a pretreatment of the nanoparticles, and the zone made up of blocks (50) and (60), representing the process of preparation of the additive as such.

In zone I or the pretreatment phase, block (10) represents the raw material, constituted of metal nanoparticles, their composites or mixtures thereof, which will be used for preparing the additive, preferably being a moist paste, although for some very specific applications that require absence of water, dry powder is preferred. As already mentioned, the nanoparticles have an average size in the range from 1 to 100 nanometers and a purity of at least 95%. This material is supplied to block (20).

Block (20) represents an operation designated "change of vehicle", in which the raw material is washed for the purpose of removing the water or solvent contained, depending on the case, and replacing it with a "compatible" solvent, i.e. it is incorporated without causing phase separation, with the solvent or thinner of the final application (the "target coating"), which in its turn will prevent the formation of lumps on coming into contact with the target coating; the process is carried out with vigorous stirring preferably for between 5 and 30 minutes, or for as long as is necessary. The mixture is stirred in turbulent conditions by means of a disperser with a shearing disk or other device that provides a peripheral speed of at least 2 m/s and up to 30 m/s as a maximum. After stirring, phase separation takes place and the process can be repeated until a residual moisture content of less than 5% is obtained in the solid phase.

When because of the nature of the solvent or thinner, and of the resin contained in the target coating, the nanoparticles might react, the need for the particles to undergo a surface treatment (16) prior to the operation of "change of vehicle" (20), using conventional surfactants compatible with the target coating, is evaluated as indicated by block (15).

The process of "change of vehicle" (20) has the purpose of ensuring that the nanoparticles will not agglomerate in the dispersion phase (50) of zone II, on being incorporated in the coating or on application of the latter on the surface to be treated.

Block (30) indicates that in the case when the residual moisture content tolerated in the additive is very low, close to zero, owing to the nature of the resin and solvents or thinners in the target coating and once the stage of "change of vehicle" (20) is completed, the residual moisture content in the solid phase is reduced by a drying process (40), taking care that the operating temperature in said drying is below the boiling point of the vehicle. The operation is continued until a residual moisture content tolerated by the target coating is obtained.

The result of operation (40) is a "dry" powder of nanoparticles, which can be stored for subsequent preparation of the additive. The product obtained by this method retains its properties during prolonged periods of storage.

If a moisture content of the order of 5% is tolerated in the final application, the drying stage represented by block (40) is omitted.

The product obtained, whether "dry" or moist, resulting from one of the two routes of the first phase of the process (25) or (45), is submitted to a process of dispersion (50), in zone II, which properly is identified with preparation of the additive ready for use in the target coating according to the present invention.

In this stage, the paste or the "dry" powder from block (20) or (40) is fed to a process of dispersion (50) in which a resin and a dispersant that are compatible with the target coating are added, according to Table 2:

TABLE 2

Recommended selection of the resin and the dispersant for preparation of the additive

| CATEGORY OF TARGET COATING | RESIN RECOMMENDED IN THE DISPERSION | DISPERSANT RECOMMENDED IN THE DISPERSION |
|---|---|---|
| Polyurethane | Polyester or aldehyde | copolymer with acid groups, alkylammonium salt of a polycarboxylic acid, alkylammonium salt of an unsaturated fatty acid, salt of unsaturated polyamine amides and acid polyesters of low molecular weight, unsaturated polyamine amide and acid polyesters of low molecular weight |
| UV curing | Epoxy-acrylate | copolymer with acid groups, alkylammonium salt of a polycarboxylic acid, alkylammonium salt of an unsaturated fatty acid, salt of unsaturated polyamine amides and acid polyesters of low molecular weight, salt of an unsaturated polyamine amide and acid polyesters of low molecular weight |
| Styrene - Acrylic | Styrene - Acrylic | ammonium salt of an acrylic copolymer, alkylammonium salt and a polyfunctional polymer of anionic character, sodium salt of an acrylic copolymer |
| Vinylic | Vinylic | ammonium salt of an acrylic copolymer, alkylammonium salt and a polyfunctional polymer of anionic character, sodium salt of an acrylic copolymer |
| Alkydalyl enamel | Alkydalyl resin | copolymer with acid groups, alkylammonium salt of a polycarboxylic acid, alkylammonium salt of an unsaturated fatty acid, salt of unsaturated polyamine amides and acid polyesters of low molecular weight, salt of an unsaturated polyamine amide and acid polyesters of low molecular weight |
| 0% Volatile organic compounds Nitro-cellulosic | Styrene - Acrylic, Vinylic, Epoxy-acrylate Stabilized alkydalyl or nitro-cellulose | ammonium salt of an acrylic copolymer, alkylammonium salt and a polyfunctional polymer of anionic character, sodium salt of an acrylic copolymer copolymer with acid groups, alkylammonium salt of a polycarboxylic acid, alkylammonium salt of an unsaturated fatty acid, salt of unsaturated polyamine amides and acid polyesters of low molecular weight, salt of an unsaturated polyamine amide and acid polyesters of low molecular weight |
| Alkydalyl | Alkydalyl of soya, coconut, lecithin | copolymer with acid groups, alkylammonium salt of a polycarboxylic acid, alkylammonium salt of an unsaturated fatty acid, salt of unsaturated polyamine amides and acid polyesters of low molecular weight, salt of an unsaturated polyamine amide and acid polyesters of low molecular weight |
| Phenolic | Phenolic resin | copolymer with acid groups, alkylammonium salt of a polycarboxylic acid, alkylammonium salt of an unsaturated fatty acid, salt of unsaturated polyamine amides and acid polyesters of low molecular weight, salt of an unsaturated polyamine amide and acid polyesters of low molecular weight |

Dispersion (50) is carried out by means of a stirrer or disperser with a peripheral speed of between 15 and 30 m/s. The viscosity of the mixture is adjusted to that of the target coating by adding solvent or thinner, which preferably is the same as will be used with the coating or at least must be compatible with it. The percentage of dispersant in the mixture is maintained at between 0.5 and 10% depending on the nanoparticles in the dry base.

The product (60) obtained from the process of dispersion (50) is the additive of the invention, and can even be, in the preferred embodiment, a formulation with up to 99 wt. % of nanoparticles.

Among the advantages of the additive obtained by the method of the invention, there is the fact that as a result of the treatment of change of vehicle in stage (20) and mixing with resins and dispersants in stage (50), the product is completely compatible with the target coating for which it was prepared by selecting the appropriate resin and dispersant in accordance with Table 2 presented above, and selection of a suitable surfactant, when necessary, moreover maintaining a high degree of homogeneity in the dispersion of nanoparticles in the formulation, so that on being added to the target coating, the additive will be incorporated easily and quickly and this ensures that the particles will maintain their homogeneity of dispersion throughout the volume and, therefore, in the coating layer after application on the surface to be protected.

Example 1

Preparation of the Additive for Use in an Organic Matrix for Use in Polyester-Based Paint 1. Start with a paste of nanoparticles of metallic silver, with a water content of 64%, with a particle size distribution $D_{10}$, 16.3 nm; $D_{50}$, 23.9 nm; $D_{90}$, 43.5 nm; measured by photon correlation spectroscopy (PCS), in equipment of type MALVERN Zetasizer Nano ZS. For purposes of illustration, 300 grams is used.
2. Pour the paste of nanoparticles into a narrow-mouth beaker of the Berzelius type, equipped with a propeller disperser, add two volumes of cellosolve butyl solvent, equal to that of the paste. Disperse for 5 minutes.
3. Separate the nanoparticles from the mother liquor, by physical means (decanting, filtration, centrifugation, etc.). Retain the liquor for analysis of physical water by the Karl Fischer method. Weigh the amount of paste of nanoparticles obtained, to calculate the water content of the paste.
4. Repeat steps 2 and 3 as many times as necessary until, in the paste of nanoparticles, a water content of less than 5%, or that accepted for the final application, is reached.
5. Steps 2 and 3 are repeated 3 more times, but now the solvent is replaced with propylene glycol acetate methyl ether.
6. In a separate vessel, dissolve 125 grams of the polyester-based resin or some other that is compatible with this system, for example, Laropal® A 81 (BASF), with 100 mL of the solvent propylene glycol acetate methyl ether. Check for complete dissolution of the resin by conventional methods.
7. Disperse the paste of nanoparticles obtained in step 5, in the solution of resin and solvent from step 6, add 20 g of dispersant, from the selection recommended in Table 2. A peripheral speed of between 15 and 30 m/s for a period of between 5 and 30 minutes is recommended. Verify dispersion of the paste by known conventional methods.
8. Dilute the rest of the resin (375 grams) in the paste dispersed in step 7, add a further 400 mL of solvent propylene glycol acetate methyl ether. This is carried out for 1 hour at a peripheral speed of 5 m/s.
9. Adjust the paste to 1000 grams with solvent propylene glycol acetate methyl ether. Verify, in the paste, the percentage of nanoparticles, the percentage of total solids, density, viscosity, morphology by microscopy and physical moisture by Karl Fischer.

Example 2

Preparation of the Additive for Use in an Organic Matrix for Use in Polyurethane-Based Paint 1. Start with a paste of nanoparticles of metallic silver, with a water content of 64%, with a particle size distribution $D_{10}$, 16.3 nm; $D_{50}$, 23.9 nm; $D_{90}$, 43.5 nm; measured by photon correlation spectroscopy (PCS), in equipment of type MALVERN Zetasizer Nano ZS. For purposes of illustration, 300 grams is used.
2. Pour the paste of nanoparticles into a narrow-mouth beaker of the Berzelius type, equipped with a propeller disperser, add two volumes of cellosolve butyl solvent, equal to that of the paste. Disperse for a period of 5 minutes.
3. Separate the nanoparticles from the mother liquor, by physical means (decanting, filtration, centrifugation, etc.). Retain the liquor for analysis of physical water by the Karl Fischer method. Weigh the amount of paste of nanoparticles obtained, to calculate the water content of the paste.
4. Repeat steps 2 and 3 as many times as is necessary until, in the paste of nanoparticles, a water content of less than 5% or that accepted for the final application is reached.
5. In a separate vessel dissolve 125 grams of the polyurethane-based resin or some other that is compatible with this system, for example, Laropal® A 81 (BASF), with 100 mL of the cellosolve butyl solvent. Check for complete dissolution of the resin by conventional methods.
6. Disperse the paste of nanoparticles obtained in step 5, in the solution of resin and solvent from step 6, add 20 g of dispersant, from the selection recommended in Table 2. A peripheral speed of between 15 and 30 m/s for a period of between 5 and 30 minutes is recommended. Verify the dispersion of the paste by known conventional methods.
7. Dilute the rest of the resin (375 grams) in the paste dispersed in step 7, add a further 400 mL of cellosolve butyl solvent. This is carried out for 1 hour at a peripheral speed of 5 m/s.
8. Adjust the paste to 1000 grams with cellosolve butyl solvent. Verify, in the paste, the percentage of nanoparticles, the percentage of total solids, density, viscosity, morphology by microscopy and physical moisture by Karl Fischer.

As will be evident to a person skilled in the art, the process described for the production of the additive according to the present invention can be used for obtaining suitable additives that confer desired properties in the final application, by selecting the compound or mixture of compounds according to Table 1, without the need to modify the Having described the invention, what is considered novel and therefore claimed as property is:

1. An additive to be incorporated in coatings which transfer to surfaces at least one of the following properties: biocidal, ultraviolet radiation protection and fire protection, said additive comprising: an active agent being metal nanoparticles, a solvent (vehicle), a dispersant and a resin, wherein:
   the active agent has an average particle size in the range from 1 nanometer to 100 nanometers and a purity of at least 95%,
   wherein the resin comprises: alkydalyl resin, and the dispersant comprises at least one selected of group consisting of: copolymer with acid groups, alkylammonium salt of a polycarboxylic acid, alkylammonium salt of an unsaturated fatty acid, salt of unsaturated polyamine amides and acid polyesters of low molecular weight, salt of an unsaturated polyamine amide and acid polyesters of low molecular weight;
   and wherein the active agent, the solvent, the resin and the dispersant are compatible with the coating for which the additive is prepared;
   in order that said additive is quickly and easily integrated to said coating by means of adjusting the viscosity of said additive to that of said coating by addition of solvent or thinner.

2. The additive of claim 1, wherein the percentage of the dispersant is maintained between 0.5% and 10% based on the active agent.

3. The additive of claim 1, wherein the active agent is selected from a group consisting of Ag, Cu, ZnO, AgS, and mixtures thereof.

4. An additive to be incorporated in coatings which transfer to surfaces at least one of the following properties: biocidal, ultraviolet radiation protection and fire protection, said additive comprising: an active agent being metal nanoparticles, a solvent (vehicle), a dispersant and a resin, wherein:
   the active agent has an average particle size in the range from 1 nanometer to 100 nanometers and a purity of at least 95%,
   wherein the resin comprises one selected of: stabilized alkydalyl or nitro-cellulose, and the dispersant comprises at least one selected of group consisting of: copolymer with acid groups, alkylammonium salt of a polycarboxylic acid, alkylammonium salt of an unsaturated fatty acid, salt of unsaturated polyamine amides and acid polyesters of low molecular weight, salt of an unsaturated polyamine amide and acid polyesters of low molecular weight;
   and wherein the active agent, the solvent, the resin and the dispersant are compatible with the coating for which the additive is prepared;
   in order that said additive is quickly and easily integrated to said coating by means of adjusting the viscosity of said additive to that of said coating by addition of solvent or thinner.

5. An additive to be incorporated in coatings which transfer to surfaces at least one of the following properties: biocidal, ultraviolet radiation protection and fire protection, said additive comprising: an active agent being metal nanoparticles, a solvent (vehicle), a dispersant and a resin, wherein:
   the active agent has an average particle size in the range from 1 nanometer to 100 nanometers and a purity of at least 95%,
   wherein the resin comprises one selected of: alkydalyl of soya, coconut, lecithin, and the dispersant comprises at least one selected of group consisting of: copolymer with acid groups, alkylammonium salt of a polycarboxylic acid, alkylammonium salt of an unsaturated fatty acid, salt of unsaturated polyamine amides and acid polyesters of low molecular weight, salt of an unsaturated polyamine amide and acid polyesters of low molecular weight;
   and wherein the active agent, the solvent, the resin and the dispersant are compatible with the coating for which the additive is prepared;
   in order that said additive is quickly and easily integrated to said coating by means of adjusting the viscosity of said additive to that of said coating by addition of solvent or thinner.

6. An additive to be incorporated in coatings which transfer to surfaces at least one of the following properties: biocidal, ultraviolet radiation protection and fire protection, said additive comprising: an active agent being metal nanoparticles, a solvent (vehicle), a dispersant and a resin, wherein:
   the active agent has an average particle size in the range from 1 nanometer to 100 nanometers and a purity of at least 95%,
   wherein the resin comprises: phenolic resin, and the dispersant comprises at least one selected of group consisting of: copolymer with acid groups, alkylammonium salt of a polycarboxylic acid, alkylammonium salt of an unsaturated fatty acid, salt of unsaturated polyamine amides and acid polyesters of low molecular weight, salt of an unsaturated polyamine amide and acid polyesters of low molecular weight;
   and wherein the active agent, the solvent, the resin and the dispersant are compatible with the coating for which the additive is prepared;
   in order that said additive is quickly and easily integrated to said coating by means of adjusting the viscosity of said additive to that of said coating by addition of solvent or thinner.

7. The additive of claim 1, wherein said additive contains up to 99 wt. % of nanometric compound as active agent.

8. The additive of claim 4, wherein said additive contains up to 99 wt. % of nanometric compound as active agent.

9. The additive of claim 5, wherein said additive contains up to 99 wt. % of nanometric compound as active agent.

10. The additive of claim 6, wherein said additive contains up to 99 wt. % of nanometric compound as active agent.

11. The additive of claim 4, wherein the percentage of the dispersant is maintained between 0.5% and 10% based on the active agent.

12. The additive of claim 5, wherein the percentage of the dispersant is maintained between 0.5% and 10% based on the active agent.

13. The additive of claim 6, wherein the percentage of the dispersant is maintained between 0.5% and 10% based on the active agent.

14. The additive of claim 4, wherein the active agent is selected from a group consisting of Ag, Cu, ZnO, AgS, and mixtures thereof.

15. The additive of claim 5, wherein the active agent is selected from a group consisting of Ag, Cu, ZnO, AgS, and mixtures thereof.

16. The additive of claim 6, wherein the active agent is selected from a group consisting of Ag, Cu, ZnO, AgS, and mixtures thereof.

* * * * *